United States Patent
Patel et al.

(10) Patent No.: US 8,913,628 B2
(45) Date of Patent: Dec. 16, 2014

(54) MEDIUM ACCESS CONTROL (MAC) PROTOCOL FOR BODY AREA NETWORKS

(75) Inventors: Maulin D. Patel, Tuckahoe, NY (US); Richard Chen, Croton-On-Hudson, NY (US)

(73) Assignee: Koninklijke Philips N.V., Eindhoven (NL)

( * ) Notice: Subject to any disclaimer, the term of this patent is extended or adjusted under 35 U.S.C. 154(b) by 455 days.

(21) Appl. No.: 13/058,003

(22) PCT Filed: Aug. 7, 2009

(86) PCT No.: PCT/IB2009/053492
§ 371 (c)(1),
(2), (4) Date: Apr. 6, 2011

(87) PCT Pub. No.: WO2010/018517
PCT Pub. Date: Feb. 18, 2010

(65) Prior Publication Data
US 2011/0182262 A1 Jul. 28, 2011

Related U.S. Application Data

(60) Provisional application No. 61/087,745, filed on Aug. 11, 2008.

(51) Int. Cl.
H04L 12/43 (2006.01)
H04W 74/04 (2009.01)
H04B 13/00 (2006.01)
H04B 7/26 (2006.01)
H04W 84/10 (2009.01)
H04W 48/08 (2009.01)
H04W 28/26 (2009.01)
A61B 5/00 (2006.01)
H04W 72/04 (2009.01)

(52) U.S. Cl.
CPC .............. *H04W 74/04* (2013.01); *H04W 84/10* (2013.01); *H04W 48/08* (2013.01); *H04W 28/26* (2013.01); *A61B 5/0024* (2013.01); *H04B 13/005* (2013.01); *A61B 5/0022* (2013.01); *H04W 72/0446* (2013.01); *H04B 7/2656* (2013.01)
USPC ........................................... 370/458; 370/349

(58) Field of Classification Search
CPC ........................... H04W 74/04; H04W 13/005
USPC ......... 370/349, 235, 314, 312, 322, 329, 341, 370/348, 347, 443, 431, 445, 458
See application file for complete search history.

(56) References Cited

U.S. PATENT DOCUMENTS

| | | | | |
|---|---|---|---|---|
| 5,355,374 | A * | 10/1994 | Hester et al. | 370/461 |
| 7,110,380 | B2 * | 9/2006 | Shvodian | 370/336 |
| 7,496,081 | B2 * | 2/2009 | Salokannel et al. | 370/348 |
| 7,668,147 | B2 * | 2/2010 | Lindsay et al. | 370/347 |
| 2003/0174664 | A1 | 9/2003 | Benveniste | |
| 2005/0180385 | A1 | 8/2005 | Jeong | |
| 2010/0272076 | A1 * | 10/2010 | Cavalcanti | 370/336 |

* cited by examiner

*Primary Examiner* — Brenda H Pham
(74) *Attorney, Agent, or Firm* — Larry Liberchuk

(57) ABSTRACT

A method (600) for controlling access to a wireless medium in a network. The method comprises dividing an access time to the wireless medium into fixed and repeated time rounds (300), wherein each time round includes a plurality of superframes (310) and each superframe includes a fixed number of time slots (420) (S610); allocating a global beacon period (530) within a time round (S620); and reserving subframes (410) within each superframe (300), wherein master devices can access the wireless medium at least during the reserved subframes (S630).

12 Claims, 5 Drawing Sheets

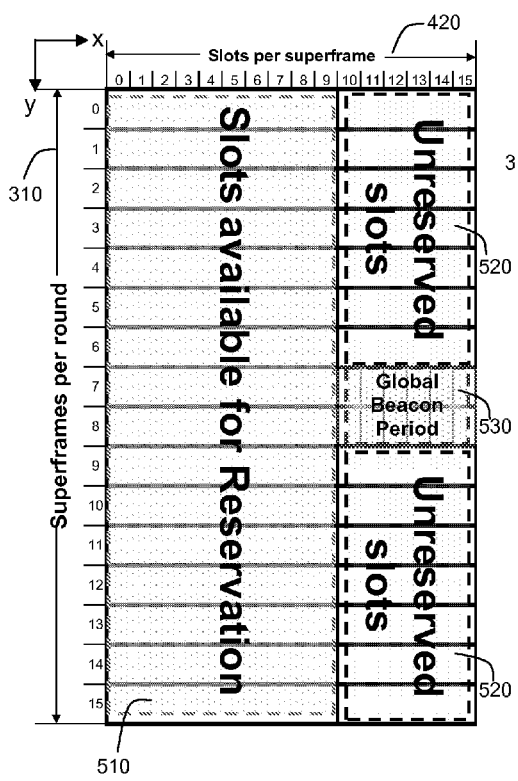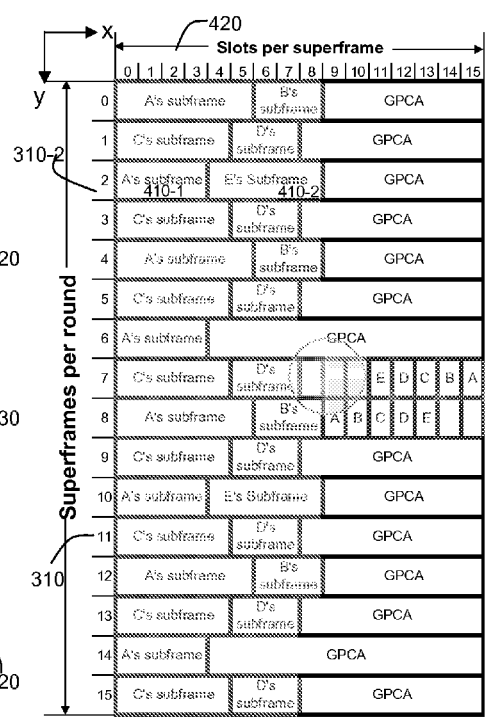
Figure 5A
Figure 5B

MEDIUM ACCESS CONTROL (MAC) PROTOCOL FOR BODY AREA NETWORKS

This application claims the benefit of U.S. Provisional Application No. 61/087,745 filed on Aug. 11, 2008.

The invention generally relates to medium access control (MAC) protocols utilized in wireless networks and, more particularly, to MAC protocols utilized in low power wireless sensor networks such as body area networks (BANs).

A body area network (BAN) is primarily designed for permanent monitoring and logging of vital signs. An exemplary BAN, shown in FIG. 1, includes multiple nodes (or devices) 120 which are typically sensors that can be either wearable or implantable into the human body. The nodes 120 monitor vital body parameters and movements, and communicate with each other over a wireless medium. The nodes 120 can transmit data from a body to one or more devices 130 from where the data can be forwarded, in real-time, to a hospital, clinic or elsewhere over a local area network (LAN), a wide area network (WAN), a cellular network, and the like.

The requirements for designing BANs include energy efficiency of nodes 120, scalability, integration, interference mitigation, coexistence, high quality of service (QoS), and security. Efficient energy consumption can be achieved by optimally duty cycling a receiver node (i.e., a node receiving data) between a listen state and a sleep state. In the sleep state the transceiver of the node is turned off, thereby saving energy. A duty cycling is performed by a MAC protocol with the aim of minimizing idle listening time, overhearing time, transmission collisions and controlling overhead.

In the related art several MAC protocols are disclosed for wireless networks. For example, the IEEE 802 standards committee has developed a family of standards for wireless local and personal area networks, such as the IEEE 802.11 standard designed for wireless local area networks (WLANs) and the IEEE 802.15.4 standard designed for wireless personal area networks (WPANs). None of these protocols is a suitable candidate for wireless BANs. For instance, the IEEE 802.15.4 standard defines a MAC protocol for short range transmissions which suffers from several shortcomings.

Specifically, the IEEE 802.15.4 standard beaconing mode supports star and tree network topologies. This centralized architecture suffers from a single point of failure which makes it unsuitable for BANs. Beaconing devices in an IEEE 802.15.4 based network are active during fixed and a-priori determined time periods. This results in either overprovisioning and waste of energy or underprovisioning and limited QoS. As duty cycle requirements of BAN nodes vary over time, the fixed duty cycling approach of IEEE 802.15.4 standard is not suitable for the BAN.

In addition, the IEEE 802.15.4 standard does not support mobility and co-existence, as it is designed for static and low data rate wireless sensor networks (WSNs). Multiple co-located IEEE 802.15.4 based networks operating on the same medium do not coordinate medium access. Therefore, transmissions of beacons and data frame can collide. The IEEE 802.15.4 standard neither detects overlapping superframes nor resolves systematic collisions. For at least the shortcomings described above, the IEEE 802.15.4 standard is inefficient to perform medium access control in BANs.

Certain embodiments of the present invention include a method for controlling access to a wireless medium in a network. The method comprises dividing an access time to the wireless medium into fixed and repeated time rounds, wherein each time round includes a plurality of superframes and each superframe includes a fixed number of time slots; allocating a global beacon period within a time round; and reserving subframes within each superframe, wherein master devices can access the wireless medium at least during the reserved subframes.

Certain embodiments of the invention also include a computer readable medium having stored thereon computer executable code that when executed causing a processor to perform the process of controlling access to a wireless medium in a network. The process comprises dividing an access time to the wireless medium into fixed and repeated time rounds, wherein each time round includes a plurality of superframes and each superframe includes a fixed number of time slots; allocating a global beacon period within a time round; and reserving subframes within each superframe, wherein master devices can access the wireless medium at least during the reserved subframes.

Certain embodiments of the invention further include a wireless data communication system. The system comprises a plurality of master devices; and a plurality of slave devices, wherein each master device communicates with an assigned set of slave devices during subframes reserved for the master device, each subframe being part of a superframe included in a time round.

Certain embodiments of the invention also include a device forming a frame structure of fixed and repeated time rounds for controlling medium access in a wireless network. The frame structure comprises a plurality of superframes, wherein each superframe includes a fixed number of time slots, wherein the time slots within each superframe are reserved for subframes and a global prioritized contention access (GPCA), wherein time slots within each subframe are reserved for communication between a master device and one or more slave devices and for a local prioritized contention access (LPCA).

The subject matter that is regarded as the invention is particularly pointed out and distinctly claimed in the claims at the conclusion of the specification. The foregoing and other features and advantages of the invention will be apparent from the following detailed description taken in conjunction with the accompanying drawings.

FIGS. 5A and 5B are diagrams for illustrating a two-dimensional representation of a time round.

Figure 1:
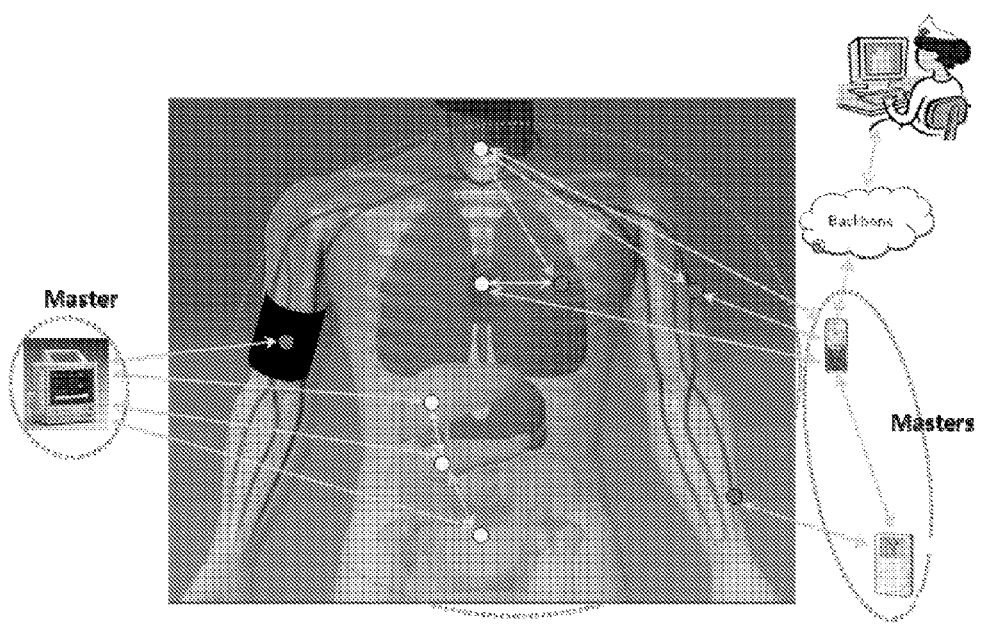
FIG. 1 is a schematic diagram of a body area wireless network.

It is important to note that the embodiments disclosed by the invention are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in plural and vice versa with no loss of generality. In the drawings, like numerals refer to like parts through several views.

Figure 2:
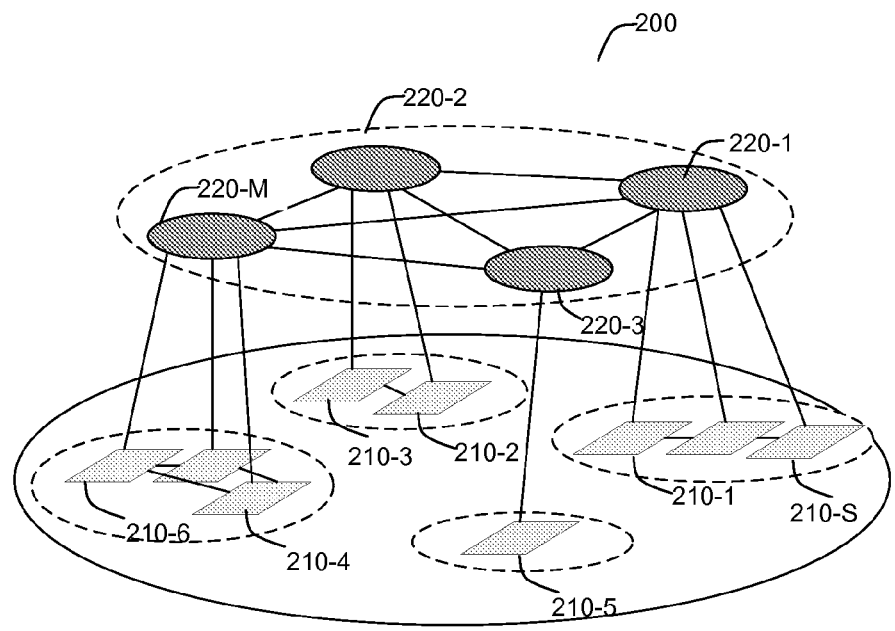
FIG. 2 illustrates a topology of a body area network constructed in accordance with an embodiment of the invention.

FIG. 2 shows a topology of a body area network (BAN) 200 constructed in accordance with an embodiment of the invention. The BAN 200 includes two tiers of devices: slave devices 210-1 through 210-S and master devices 220-1 through 220-M. Typically, the slave devices 210-1 to 210-S are implantable, swallowable or disposable and characterized by having low energy budgets and limited resources (processing power, memory). On the other hand, the master devices 220-1 to 220-M are wearable, can be recharged frequently and, therefore, have higher energy budgets and more resources than the slave devices.

A master device 220-X (where X is an integer equal to or greater than 1) manages one or more slave devices 210-Y (where Y is an integer equal to or greater than 1). To this end, the master devices 220-1 to 220-M transmit periodic beacons for synchronization, requesting medium reservation, and announcing broadcast/multicast. Based on the information exchanged by the periodic beacons, the master devices 220-1 to 220-M derive a conflict-free reservation schedule to enable QoS support. In addition, the master devices 220-1 to 220-M detect the presence of another BAN in the vicinity to support co-existence. The slave devices 210-1 and 210-S track beacons of their respective master device 220-X, transmit and receive data.

That is, one or more slave devices 210-1 to 210-S are associated with one or more master devices 220-1 to 220-M. This type of architecture is ideal for the coexistence of multiple BANs running different applications. For example, a patient wears electrocardiogram (ECG), electromyogram (EMG), electroencephalogram (EEG), $O_2$, $CO_2$ and glucose level sensors, which are the slave devices 210-1 to 210-S. In this case, four different and independent master devices 220-X can be utilized. A first master device for ECG recording, a second master device for EMG recording, a third master device for EEG recording, and a fourth device for $O_2$, $CO_2$ and glucose level monitoring. ECG leads, EMG electrodes, EEG electrodes, and $O_2$, $CO_2$ and glucose level sensors are examples of slave devices 210-Y which report data to their respective master devices.

Master and slave devices can coexist and share the same medium with no central control device. All the master devices 220-1 to 220-M synchronize the medium access and reservation. Two neighboring master devices 220-X and 220-Y can directly communicate with each other. A master device 220-X can directly communicate with its slave devices 220-1 to 220-S, and vice versa. Two neighboring slave devices 210-X and 210-Y, managed by the same master device 210-Z, can directly communicate with each other. That is, the disclosed network topology enables peer-to-peer communication between two slave devices.

It should be noted that a group of devices can periodically elect one device to become the master device and other devices can act as slave devices to balance energy consumption. It is appreciated that devices, such as cell phones, bed side monitors, ECG aggregators, and the like can be utilized as master devices, whereas wrist watches, ECG electrodes, blood pressure (BP) monitors, and camera-pills can be function as slave devices.

As discussed above, master and slave devices share the same wireless medium. In accordance with the principles of the invention master devices 220-1 to 220-S coordinate access to the shared medium using a distributed beaconing process, thereby providing a robust network protected from a single point of failure. In accordance with certain embodiments of the invention several data structures are defined to facilitate the shared medium access by master and slave devices. The data structures include a time round, a superframe, and a subframe.

Figure 3:
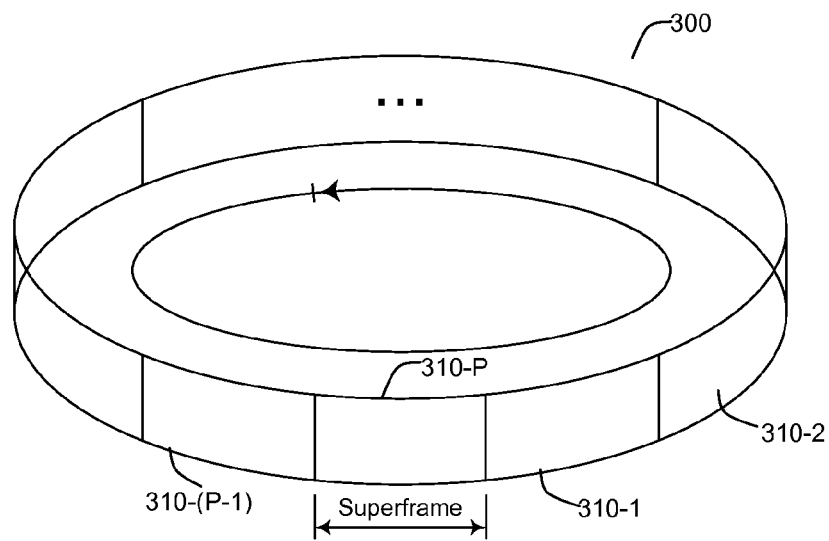
FIG. 3 is a schematic diagram for illustrating a time round constructed in accordance with an embodiment of the invention.

As shown in FIG. 3, a time round 300 includes a predefined number of superframes 310-1 to 310-P (where P is an integer number greater than 1). The access to the medium is divided into fixed and repeated duration time rounds. Repeated time rounds enable the devices to reduce the frequency of beacon transmission and, therefore, to control overhead.

Figure 4:
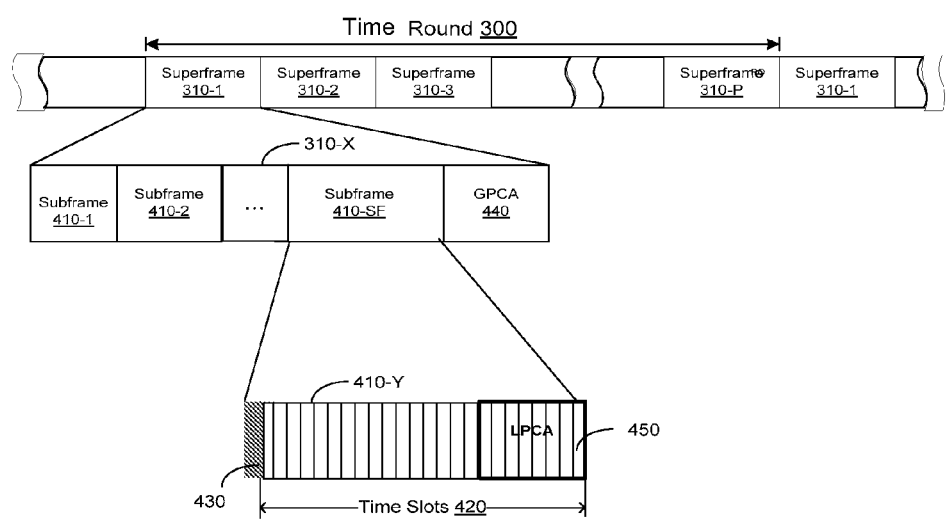
FIG. 4 is a schematic diagram for illustrating micro organization of a time round, a superframe, and a subframe constructed in accordance with an embodiment of the invention.

As depicted in FIG. 4, a superframe 310-X (where X is an integer number equal to or greater than 1) includes a configurable number of subframes 410-1 to 410-SF. The length of a subframe 410-Y (where Y is an integer number equal to or greater than 1) is variable and determined by a master device that "owns" that subframe. Each superframe 310-X has a fixed length and number of configurable time slots (collectively referred to as time slots 420). Each time slot has the same size and serves as the basic unit of medium reservation. Each subframe 410-Y begins with a local beacon 430 transmitted by a master device 220-Z (where Z is an integer number equal to or greater than 1). The slave devices 210-Y associated with a master device 220-Z listen to the local beacon 430 to synchronize and to learn if a master device 220-Z has any message pending for them. A local beacon 430 also announces time slots allocation information and scheduled times for local (between a master device and its slave devices) broadcast/multicast transmission. The slave devices 210-1 to 210-S do not listen to all the subframes 410, thus enabling them to sleep for prolong periods of time.

In accordance with one embodiment, a local beacon 430 also carries the locations of imminent subframes 410 of other master devices 220-X. This allows a slave device 210-Y which overhears a local beacon 430 sent from other master devices 220-X to determine the exact location of a subframe of its master device 220-Z. Thus, a slave device 210-Y waking up out of turn (e.g., due to clock drift or stale schedule) can return to a sleep state. This approach significantly minimizes the idle listening time.

The medium reservation is described with reference to FIGS. 5A and 5B that show an exemplary and non-limiting two-dimensional representation of a time round 300. The X-axis represents the time slots 420 per superframe and the Y-axis represents the superframes 310 per a time round 300. In the example provided in FIGS. 5A and 5B, there are 16 time slots per superframe and 16 superframes per round.

Master devices 220-1 to 220-M can reserve time slots during which they have exclusive right to access the medium. In certain embodiments, the time slots 420 are reserved according to the traffic load and latency requirement. As illustrated in FIG. 5A, a group 510 of time slots is the reserved time slots, and a second group 520 of time slots is not reserved. Typically, the reserved time slots are used for periodic or high priority traffic, and the unreserved time slots are utilized for on-demand traffic. A global time period 530 of time slots is utilized for transmitting global beacons.

Each master device 220-Z requests time slots 420 for its purposes and also on behalf of its one or more slave devices 210-Y. Time slots 420 requested by a master device 220-Z during a superframe 310-X are allocated contiguously, thereby forming a subframe 410-Y within a superframe 310-X. As shown in FIG. 5B, a superframe 310-2 includes two subframes 410-1 and 410-2 respectively allocated to master devices "A" and "E". As demonstrated in FIG. 5B, the duration of a subframe varies according to the slot reservation.

The global beacon period 530 is required to facilitate a periodic synchronization of master devices 220-Z. In a preferred embodiment of the invention the global beacon period 530 is located in the middle of a time round. The master devices 220-1 to 220-M listen to the global beacon period 530 and send global beacons in their allocated time slots to synchronize and exchange reservation requests. Global beacons are also used to discover neighbors and network topology and to schedule broadcast/multicast data transmissions.

A new schedule of subframe transmissions is derived based on reservation requests received from the master devices 220-1 to 220-M during the global beacon period 530 and becomes effective at the beginning of the next time round. Since the slave devices 210-1 to 210-S do not participate in the global beacon exchange, they are unaware of impending changes in the schedule. Therefore, master devices communicate the changed schedule to their slaves before the changes become effective. To this end, the global beacon period 530 is located in the middle of a time round, enabling the master devices 220-1 to 220-M to inform their slave devices about new schedules in the current round.

Unreserved slots in the group 520 can be accessed using a global prioritized contention access (GPCA) or local prioritized contention access (LPCA) mechanism. Specifically, unreserved time slots in superframes 310 can be accessed using the GPCA mechanism, while slots in the subframes 410 can be accessed using the LPCA mechanism.

Contention-based access is well suited for on-demand or aperiodic data traffic and can be used as fallback access mechanism, if reserved time slots are unusable due to interference or reservation conflicts. Acquiring additional time slots to accommodate increased traffic demand may incur significant delays. Until the time slots become available for reservation based access, the contention based access can be used to transmit the additional traffic. If all the time slots are made available for reservation, then once all the time slots are allocated, other master devices may be denied the access to the medium. Therefore, in accordance with the principles of the invention, a superframe may include a GPCA period and a LPCA period that may be allocated within the subframe. During these periods, the master and slave devices can contend to access the medium. Specifically, during a GPCA period any device can contend for the medium, while during a LPCA period, only the owner of the subframe, its slaves and communicating peers can contend for the medium. FIG. 4 shows an example of a superframe 310-X and a subframe 410-Y that respectively include a GPCA period 440 and a LPCA period 450.

Figure 6:
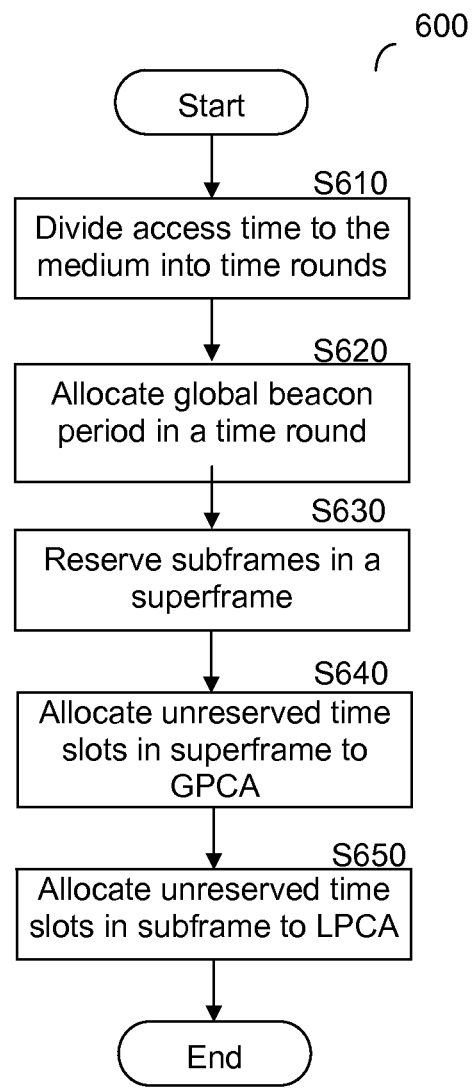
FIG. 6 is a flowchart for describing the method for controlling access to a wireless medium of a BAN implemented in accordance with an embodiment of the invention.

FIG. 6 shows an exemplary and non-limiting flowchart 600 describing the method for controlling access to a wireless medium of a BAN implemented in accordance with an embodiment of the invention.

At S610, the access time to the medium is divided into time rounds. A time round includes a plurality of superframes. In an exemplary embodiment the duration of a time round is a couple of seconds, and the duration of a superframe is tens of milliseconds. At S620, a global beacon period is allocated, preferably in the middle of the time round. The global beacon period is utilized to transmit global beacons by master devices in the BAN. At S630, subframes within a superframe are reserved for master devices. As mentioned above, a subframe comprises time slots which are reserved for a particular master device to communicate with its slave device(s). Then, each master device can allocate time slots within its allocated subframes to its slave device(s). At S640, unreserved time slots in a superframe are allocated to a GPCA in which devices can communicate with each other using the contention based access mechanism. At S650, unreserved time slots in a subframe are allocated to a LPCA in which slave devices of a respective master device can communicate with each other or with their master device using the contention based access mechanism.

It should be appreciated that the medium access control method described herein provides an adaptive duty cycling that closely matches the latency requirement and the traffic load of the network. That is, a master device remains active only when it transmits its subframes and during the global beacon period. A master device can return to sleep earlier than the end of their subframe if the medium remains idle for a predefined period of time in which none of its neighbors intends to transmit the data. The slave devices are active only for receiving their master devices local beacons and for transmitting and receiving data. The protocol allows prolong sleep periods for slave devices.

The foregoing detailed description has set forth a few of the many forms that the invention can take. It is intended that the foregoing detailed description be understood as an illustration of selected forms that the invention can take and not as a limitation to the definition of the invention. It is only the claims, including all equivalents that are intended to define the scope of this invention.

Most preferably, the principles of the invention are implemented as any combination of hardware, firmware and software. Moreover, the software is preferably implemented as an application program tangibly embodied on a program storage unit or computer readable medium. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit.

What is claimed is:

1. A method for controlling access to a wireless medium in a body area network having two tiers of devices including a plurality of master devices and a plurality of slave devices, the method comprising:
    dividing an access time to the wireless medium into fixed and repeated time rounds, wherein each time round includes a plurality of superframes and each superframe includes a fixed number of time slots;
    allocating a global beacon period within a time round for transmission of global beacons to the master devices; and
    reserving subframes within each superframe, wherein master devices can access the wireless medium at least during the reserved subframes to communicate with one or more slave devices.

2. The method of claim 1, further comprising allocating unreserved time slots in a superframe for a global prioritized contention access (GPCA).

3. The method of claim 1, further comprising reserving time slots within each subframe in which slave devices can communicate with a master device.

4. The method of claim 3, further comprising allocating unreserved time slots in a subframe for a local prioritized contention access (LPCA) in order that slave devices associated with the master device can communicate with each other.

5. The method of claim 3, wherein each master device communicates with a set of slave devices associated with the master device.

6. The method of claim 5, wherein a local beacon is transmitted by a master device to announce time slots allocated within a subframe for the set of slave devices associated with said master device.

7. The method of claim 1, wherein the global beacon period is in the middle of the time round.

8. The method of claim 7, wherein global beacons are transmitted by master devices during the global beacon period.

9. The method of claim 8, wherein a global beacon is utilized for at least one of: synchronizing and exchanging reservation requests, discovering neighbors and network topology, and scheduling data transmissions.

10. The method of claim 1, the number of superframes within a time round and the number of time slots within a superframe are preconfigured.

11. A non-transitory computer readable medium having stored thereon computer executable code, which when executed by a processor, causes the processor to control access to a wireless medium in a body area network having two tiers of devices including a plurality of master devices and a plurality of slave devices, comprising:

dividing an access time to the wireless medium into fixed and repeated time rounds, wherein each time round includes a plurality of superframes and each superframe includes a fixed number of time slots;

allocating a global beacon period within a time round for transmission of global beacons to the master devices; and reserving subframes within each superframe, wherein master devices can access the wireless medium at least during the reserved subframes to communicate with one or more slave devices.

12. A device comprising:

a memory; and a processor configured to form a frame structure of fixed and repeated time rounds for controlling access to a wireless body area network having two tiers of devices including a plurality of master devices and a plurality of slave devices, wherein each time round includes a plurality of superframes, and each superframe includes a fixed number of time slots, wherein the time slots within each superframe are reserved for subframes and a global prioritized contention access (GPCA), each time round including a global beacon period allocated for transmission of global beacons to the master devices, and the subframe time slots are reserved for communication between a master device and one or more slave devices, and for a local prioritized contention access (LPCA).

* * * * *